United States Patent
Wang (10) Patent No.: US 9,370,422 B2
(45) Date of Patent: Jun. 21, 2016

(54) EXPANDABLE RADIOPAQUE MARKER FOR TRANSCATHETER AORTIC VALVE IMPLANTATION

(75) Inventor: Huisun Wang, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 441 days.

(21) Appl. No.: 13/552,929

(22) Filed: Jul. 19, 2012

(65) Prior Publication Data
US 2013/0073032 A1    Mar. 21, 2013

Related U.S. Application Data

(60) Provisional application No. 61/512,490, filed on Jul. 28, 2011.

(51) Int. Cl.
*A61F 2/24* (2006.01)

(52) U.S. Cl.
CPC .............. *A61F 2/2436* (2013.01); *A61F 2/243* (2013.01); *A61F 2/246* (2013.01); *A61F 2/2427* (2013.01); *A61F 2250/0098* (2013.01)

(58) Field of Classification Search
USPC ........................................................ 623/2.11
See application file for complete search history.

(56) References Cited

U.S. PATENT DOCUMENTS

| | | |
|---|---|---|
| 4,423,730 A | 1/1984 | Gabbay |
| 4,471,777 A | 9/1984 | McCorkle, Jr. |
| 4,546,759 A | 10/1985 | Solar |
| 4,575,371 A | 3/1986 | Nordqvist et al. |
| 5,090,958 A | 2/1992 | Sahota |
| 5,120,299 A | 6/1992 | Lombardi |
| 5,334,160 A | 8/1994 | Ellis |
| 5,411,552 A | 5/1995 | Andersen et al. |
| 5,733,325 A | 3/1998 | Robinson et al. |
| 5,795,325 A | 8/1998 | Valley et al. |
| 5,797,952 A | 8/1998 | Klein |
| 5,827,324 A | 10/1998 | Cassell et al. |
| 5,868,706 A | 2/1999 | Cox |

(Continued)

FOREIGN PATENT DOCUMENTS

| | | |
|---|---|---|
| DE | 102004062296 A1 | 7/2006 |
| EP | 1129744 A1 | 9/2001 |

(Continued)

OTHER PUBLICATIONS

International Search Report and Written Opinion for Application No. PCT/US2012/047283 dated Oct. 30, 2012.

(Continued)

*Primary Examiner* — Robert Lynch
(74) *Attorney, Agent, or Firm* — Lerner, David, Littenberg, Krumholz & Mentlik, LLP (57) ABSTRACT

A delivery device for a collapsible prosthetic heart valve includes a support shaft around which a compartment for the valve is defined, a distal sheath adapted to selectively cover and uncover the compartment and the valve, and a marker cage having a collapsed condition when the distal sheath covers the compartment and an expanded condition when the compartment is uncovered. The marker cage includes at least one rib having a radiopaque marker for determining the positioning of the valve as it is deployed. The valve may be assembled around the marker cage so that the marker cage does not interfere with the radial expansion of the valve during deployment.

19 Claims, 4 Drawing Sheets

(56) References Cited

U.S. PATENT DOCUMENTS

| | | |
|---|---|---|
| 5,924,424 A | 7/1999 | Stevens et al. |
| 5,968,068 A | 10/1999 | Dehdashtian et al. |
| 6,190,357 B1 | 2/2001 | Ferrari et al. |
| 6,214,036 B1 | 4/2001 | Letendre et al. |
| 6,231,588 B1 | 5/2001 | Zadno-Azizi |
| 6,306,141 B1 | 10/2001 | Jervis |
| 6,361,545 B1 | 3/2002 | Macoviak et al. |
| 6,375,668 B1 | 4/2002 | Gifford et al. |
| 6,482,228 B1 | 11/2002 | Norred |
| 6,607,551 B1 | 8/2003 | Sullivan et al. |
| 6,623,518 B2 | 9/2003 | Thompson et al. |
| 6,776,791 B1 | 8/2004 | Stallings et al. |
| 8,414,644 B2 | 4/2013 | Quadri et al. |
| 8,608,792 B2 | 12/2013 | Silveira et al. |
| 2002/0120323 A1 | 8/2002 | Thompson et al. |
| 2003/0023265 A1* | 1/2003 | Forber ................ 606/200 |
| 2003/0199963 A1 | 10/2003 | Tower et al. |
| 2004/0087900 A1 | 5/2004 | Thompson et al. |
| 2004/0093063 A1 | 5/2004 | Wright et al. |
| 2004/0204749 A1 | 10/2004 | Gunderson |
| 2004/0236406 A1 | 11/2004 | Gregorich |
| 2004/0267346 A1 | 12/2004 | Shelso |
| 2004/0267348 A1 | 12/2004 | Gunderson et al. |
| 2005/0020974 A1 | 1/2005 | Noriega et al. |
| 2005/0027345 A1 | 2/2005 | Horan et al. |
| 2005/0033398 A1 | 2/2005 | Seguin |
| 2005/0049667 A1 | 3/2005 | Arbefeuille et al. |
| 2005/0049674 A1 | 3/2005 | Berra et al. |
| 2005/0065590 A1 | 3/2005 | Shelso |
| 2005/0222662 A1 | 10/2005 | Thompson et al. |
| 2006/0100688 A1 | 5/2006 | Jordan et al. |
| 2006/0106415 A1 | 5/2006 | Gabbay |
| 2006/0111771 A1 | 5/2006 | Ton et al. |
| 2006/0142848 A1 | 6/2006 | Gabbay |
| 2006/0149294 A1 | 7/2006 | Argentine et al. |
| 2006/0167468 A1 | 7/2006 | Gabbay |
| 2006/0195184 A1* | 8/2006 | Lane et al. ............ 623/2.38 |
| 2006/0259120 A1 | 11/2006 | Vongphakdy et al. |
| 2006/0276872 A1 | 12/2006 | Arbefeuille et al. |
| 2007/0027534 A1 | 2/2007 | Bergheim et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0142858 A1 | 6/2007 | Bates |
| 2007/0162100 A1 | 7/2007 | Gabbay |
| 2007/0168013 A1 | 7/2007 | Douglas |
| 2007/0203561 A1 | 8/2007 | Forster et al. |
| 2007/0203575 A1 | 8/2007 | Forster et al. |
| 2007/0239271 A1 | 10/2007 | Nguyen |
| 2007/0293930 A1 | 12/2007 | Wang et al. |
| 2008/0103443 A1 | 5/2008 | Kabrick et al. |
| 2008/0114443 A1 | 5/2008 | Mitchell et al. |
| 2008/0147182 A1 | 6/2008 | Righini et al. |
| 2008/0221666 A1 | 9/2008 | Licata et al. |
| 2008/0228255 A1 | 9/2008 | Rust et al. |
| 2008/0255662 A1* | 10/2008 | Stacchino et al. ........ 623/2.36 |
| 2008/0262590 A1 | 10/2008 | Murray |
| 2008/0319526 A1* | 12/2008 | Hill ............... A61F 2/2418 623/1.24 |
| 2009/0054975 A1 | 2/2009 | del Nido et al. |
| 2009/0143851 A1* | 6/2009 | Paul, Jr. ................ 623/1.11 |
| 2009/0204197 A1 | 8/2009 | Dorn et al. |
| 2009/0222035 A1 | 9/2009 | Schneiderman |
| 2009/0228093 A1* | 9/2009 | Taylor et al. ............ 623/1.12 |
| 2009/0276027 A1 | 11/2009 | Glynn |
| 2009/0281610 A1 | 11/2009 | Parker |
| 2009/0287290 A1 | 11/2009 | Macaulay et al. |
| 2010/0131039 A1 | 5/2010 | Chau et al. |
| 2010/0145438 A1 | 6/2010 | Barone |
| 2010/0152834 A1 | 6/2010 | Hannes et al. |
| 2010/0268315 A1 | 10/2010 | Glynn et al. |
| 2010/0312325 A1 | 12/2010 | Dorn |
| 2011/0029065 A1 | 2/2011 | Wood et al. |
| 2011/0077731 A1 | 3/2011 | Lee et al. |
| 2011/0078350 A1 | 3/2011 | Carls |
| 2011/0098805 A1 | 4/2011 | Dwork et al. |
| 2011/0137401 A1 | 6/2011 | Dorn et al. |
| 2011/0172764 A1 | 7/2011 | Badhwar |
| 2011/0224678 A1 | 9/2011 | Gabbay |
| 2011/0251666 A1 | 10/2011 | Schmitt et al. |
| 2011/0251679 A1 | 10/2011 | Wiemeyer et al. |
| 2011/0257720 A1 | 10/2011 | Peterson et al. |
| 2011/0264201 A1 | 10/2011 | Yeung et al. |
| 2011/0264202 A1 | 10/2011 | Murray, III et al. |
| 2011/0288636 A1* | 11/2011 | Rolando et al. .......... 623/2.11 |
| 2011/0301685 A1 | 12/2011 | Kao |
| 2012/0078350 A1 | 3/2012 | Wang et al. |
| 2012/0123528 A1 | 5/2012 | Knippel et al. |
| 2013/0131775 A1 | 5/2013 | Hadley et al. |
| 2013/0204344 A1 | 8/2013 | Tatalovich et al. |
| 2013/0274860 A1 | 10/2013 | Argentine |

FOREIGN PATENT DOCUMENTS

| | | |
|---|---|---|
| EP | 1157673 A2 | 11/2001 |
| WO | 9620025 A1 | 7/1996 |
| WO | 9748343 A1 | 12/1997 |
| WO | 9965418 A1 | 12/1999 |
| WO | 2006069704 A2 | 7/2006 |
| WO | 2006124549 A1 | 11/2006 |
| WO | 2007002863 A2 | 1/2007 |
| WO | 2007134290 A2 | 11/2007 |
| WO | 2008031103 A2 | 3/2008 |
| WO | 2008097556 A1 | 8/2008 |
| WO | 2009062955 A1 | 5/2009 |
| WO | 2009/091509 A1 | 7/2009 |
| WO | 2009108942 A1 | 9/2009 |
| WO | 2010005524 A2 | 1/2010 |
| WO | 2010022138 A2 | 2/2010 |
| WO | 2010051025 A1 | 5/2010 |
| WO | 2010087975 A1 | 8/2010 |
| WO | 2011025945 A1 | 3/2011 |
| WO | 2012036740 A2 | 3/2012 |

OTHER PUBLICATIONS

International Search Report and Written Opinion for Application No. PCT/US2013/047891 dated Dec. 4, 2013.

International Search Report and Written Opinion for Application No. PCT/US2013/048413 dated Dec. 4, 2013.

International Search Report and Written Opinion for Application No. PCt/US2011/001218 dated Nov. 11, 2011.

International Search Report dated Feb. 2, 2012 for Application No. PCT/US2011/001446.

International Search Report for Application No. PCY/US2011/001596 dated May 8, 2012.

Japanese Office Action for Application No. 2013-519648 dated Jun. 30, 2015.

* cited by examiner

EXPANDABLE RADIOPAQUE MARKER FOR TRANSCATHETER AORTIC VALVE IMPLANTATION

CROSS-REFERENCE TO RELATED APPLICATION

The present application claims the benefit of U.S. Provisional Patent Application Ser. No. 61/512,490, filed Jul. 28, 2011, entitled "Expandable Radiopaque Marker for Transcatheter Aortic Valve Implantation," the disclosure of which is hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valves structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it may be difficult to determine the axial and rotational orientation of the valve relative to the patient's aortic annulus. Some conventional delivery systems include radiopaque markers permanently attached to the valve stent, but such markers may be expensive and may become detached from the implant during or after implantation, which may cause a risk of embolism.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

A delivery device for a collapsible prosthetic heart valve, a marker cage for use in deployment of a collapsible prosthetic heart valve, and a method of determining the position of a collapsible prosthetic heart valve in a patient are disclosed.

A delivery device for a collapsible prosthetic heart valve may include may include a support shaft around which a compartment is defined, a distal sheath adapted to selectively cover and uncover the compartment and the valve, a marker cage having a collapsed condition when the distal sheath covers the compartment and an expanded condition when the compartment is uncovered, and at least one radiopaque marker on the marker cage. The compartment may be adapted to receive the valve in an assembled condition. The marker cage may be adapted to engage the valve in the assembled condition.

Each radiopaque marker may include a material selected from the group consisting of gold, platinum, nitinol, and combinations thereof. The marker cage may be formed from a memory material tube having an aperture extending therethrough. The marker cage may have a first end fixedly connected to the support shaft and at least one rib having a fixed end connected to the first end. The marker cage may have a second end slidably connected to the support shaft, and the at least one rib may have another end connected to the second end. The marker cage may have a second end fixedly connected to the support shaft, and the at least one rib may have another end connected to the second end. The at least one rib may have a free end opposite the fixed end.

Substantially all of the at least one rib may be radiopaque or may be surrounded by a radiopaque material. The at least one rib may be adapted to be engaged between adjacent leaflets of the valve in the assembled condition. The prosthetic heart valve may include a tissue cuff having a longitudinal axis, and the at least one marker may be adapted to be oriented substantially parallel to the longitudinal axis in the assembled condition. The marker cage may have an expanded diameter that is greater than an expanded diameter of the prosthetic heart valve. The marker cage may include a plurality of ribs disposed around a longitudinal axis of the support shaft, each rib having at least one radiopaque marker, the radiopaque markers being positioned equidistantly from the longitudinal axis in an expanded condition of the marker cage.

The at least one rib may have first and second legs. The first leg may have one end connected to the first end of the marker cage and another end. The second leg may have a first end connected to the another end of the first leg and a second end. The second leg may extend substantially parallel to the support shaft when the marker cage is in the expanded condition. The marker cage may have a second end slidably connected to the support shaft. The at least one rib may further include a third leg having one end connected to the second end of the second leg and another end connected to the second end of the marker cage. The first and third legs of the at least one rib may extend in substantially opposite transverse directions to the support shaft when the marker cage is in the expanded condition.

A marker cage for use in deployment of a collapsible prosthetic heart valve may include a first end, at least one rib having one end connected to the first end, and at least one radiopaque marker. The marker cage may have a collapsed condition and an expanded condition. The marker cage may be adapted to engage the valve in an assembled condition.

Each radiopaque marker may include a material selected from the group consisting of gold, platinum, nitinol, and combinations thereof. The marker cage may be formed from a memory material tube having an aperture extending therethrough. The marker cage may further include a second end, the at least one rib having another end connected to the second end. The at least one rib may have a free end opposite the one end. Substantially all of the at least one rib may be radiopaque or may be surrounded by a radiopaque material. The marker cage may have an expanded diameter that is greater than an expanded diameter of the prosthetic heart valve. The marker cage may include a plurality of ribs disposed around a longitudinal axis, each rib having at least one radiopaque marker, the radiopaque markers being positioned equidistantly from the longitudinal axis in an expanded condition of the marker cage.

The at least one rib may have first and second legs. The first leg may have one end connected to the first end of the marker cage and another end. The second leg may have a first end connected to the another end of the first leg and a second end. The second leg may extend substantially parallel to a longitudinal axis of the marker cage when the marker cage is in the expanded condition. The marker cage may have a second end. The at least one rib may further include a third leg having one end connected to the second end of the second leg and another end connected to the second end of the marker cage. The first and third legs of the at least one rib may extend in substantially opposite transverse directions to the longitudinal axis when the marker cage is in the expanded condition.

A method of determining the position of a collapsible prosthetic heart valve in a patient may include providing a delivery device including a support shaft around which a compartment is defined, a distal sheath adapted to selectively cover and uncover the compartment, and a marker cage including at least one radiopaque marker and having a collapsed condition when the distal sheath covers the compartment and an expanded condition when the compartment is uncovered. The collapsible prosthetic heart valve may be mounted in the compartment so that the marker cage is positioned within the valve. The distal sheath may then be slid to cover the compartment and the valve, and to maintain the marker cage in the collapsed condition. The delivery device may be inserted into the patient. The delivery device may then be positioned so that the valve is positioned at a target location within the patient. The valve may be partially deployed by sliding the distal sheath to partially uncover the compartment and the valve. The position of the at least one marker relative to a native valve annulus of the patient may then be determined. The valve may be fully deployed by continuing to slide the distal sheath to fully uncover the valve, whereupon the marker cage will be in the expanded condition. Subsequently, the marker cage may be compressed to the collapsed condition by sliding the distal sheath to at least partially cover the compartment and the marker cage.

The marker cage may have a first end fixedly connected to the support shaft and at least one rib having a fixed end connected to the first end. The marker cage may include a plurality of ribs disposed around a longitudinal axis of the support shaft. Each rib may have at least one radiopaque marker. The radiopaque markers may be positioned equidistantly from the longitudinal axis in an expanded condition of the marker cage. The steps of partially deploying and fully deploying may include expanding the marker cage with each rib positioned between adjacent leaflets of the valve. The compressing step may include compressing the marker cage during a portion of the heart beat cycle when blood is flowing through the leaflets of the valve. The prosthetic heart valve may include a tissue cuff having a longitudinal axis. The steps of partially deploying and fully deploying may include expanding the marker cage with the at least one marker oriented substantially parallel to the longitudinal axis.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

Figure 1A:
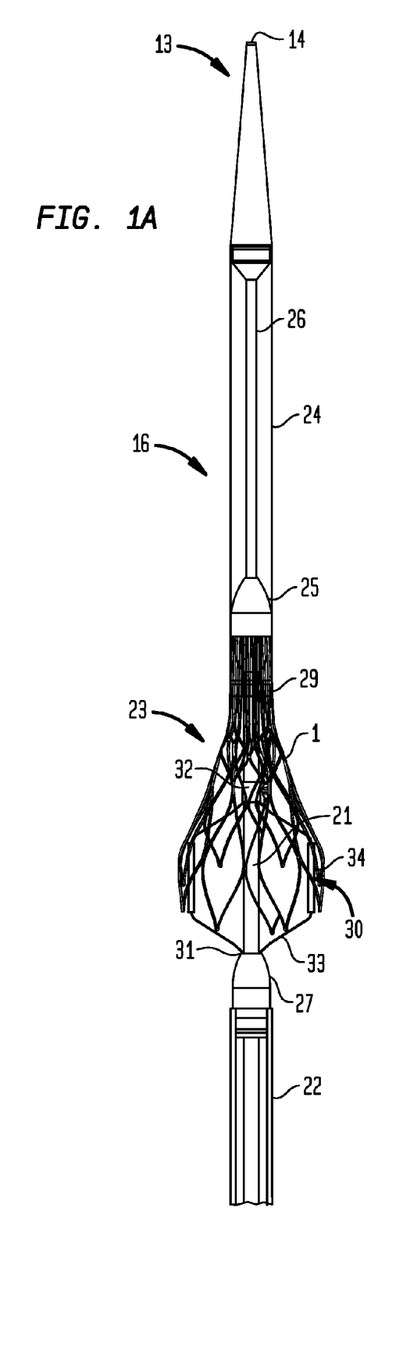
FIG. 1A is side elevational view of the distal portion of one embodiment of a transapical delivery device for a collapsible prosthetic heart valve according to the present invention.
Figure 1B:
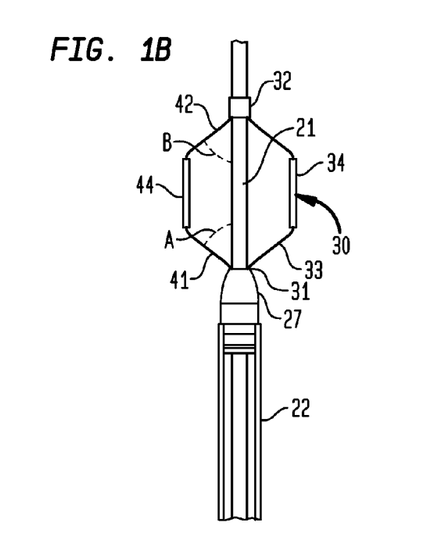
FIG. 1B is an enlarged side elevational view of a portion of the delivery device of FIG. 1A, with the valve removed to illustrate the interior of the device.
Figure 1C:
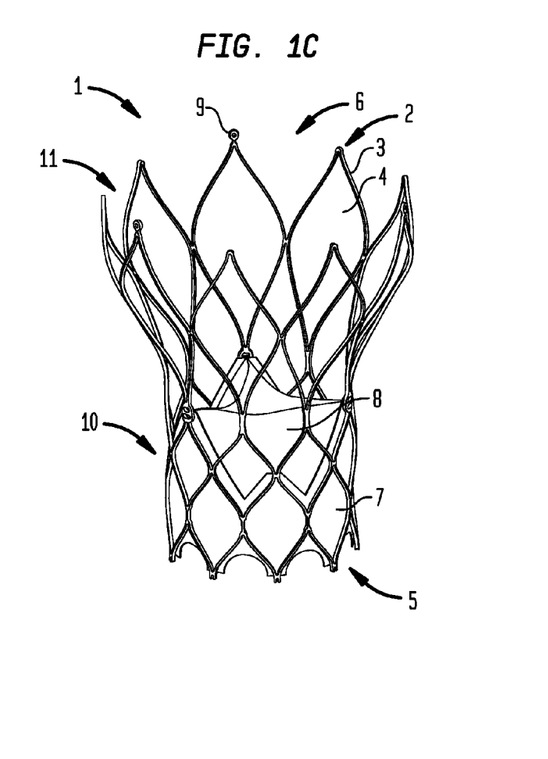
FIG. 1C is a perspective view of a collapsible prosthetic heart valve suitable for use in the delivery device of FIG. 1A.

Referring first to FIG. 1C, a collapsible prosthetic heart valve 1 includes a stent portion 2 comprising stent members 3 having a plurality of spaces 4 therebetween. The stent portion 2 includes an annulus portion 10 proximate one end 5 thereof, and an outwardly flaring aortic portion 11 proximate the other end 6 thereof. A tissue cuff 7 extends about the inner circumference of the annulus portion 10, and three leaflets 8 extend inwardly from the tissue cuff 7, with their free edges in coapting relationship. The end 6 of the stent portion 2 has a plurality of retention members 9 extending from junctions of adjacent stent members 3 and adapted to engage with acceptances in the valve delivery device, as will be described below.

Referring to FIG. 1A, an exemplary transapical delivery device 13 for the collapsible prosthetic heart valve 1 extends from an atraumatic tip 14 at the distal end of the device to a proximal end (not shown), and includes a catheter assembly 16 for delivering the heart valve to and deploying the heart valve at a target location. The catheter assembly 16 is adapted to receive the collapsible prosthetic heart valve 1 in an assembled condition in a compartment 23 defined around a support shaft 21. A distal sheath 24 is operable for sliding movement between a closed position covering the prosthetic heart valve 1 and maintaining it in a collapsed condition, and an open position for deployment of the valve.

The support shaft 21 extends between a pair of spaced retainers 25 and 27 affixed thereto and defining the ends of the compartment 23. The retainer 25 is adapted to receive the retention members 9 of the prosthetic heart valve 1 so as to hold the aortic end of the heart valve in assembled relationship with the delivery device 13. The delivery device further includes an outer shaft 22, the distal end of which is connected to the retainer 27, and the proximal end of which can optionally be connected to a hub (not shown) that can be held by a user when sliding the distal sheath 24 relative to the support shaft 21. An inner shaft 26 extends from the proximal end of the delivery device through the outer shaft 22 and the support shaft 21 for connection to the atraumatic tip 14.

The distal sheath 24 surrounds the support shaft 21 when the distal sheath is in the closed position, and is slidable relative to the support shaft such that it can selectively cover or uncover compartment 23. The distal sheath 24 is connected at its distal end to the atraumatic tip 14, such that sliding movement of the inner shaft 26 controls the movement of the distal sheath both proximally and distally. A proximal edge 29 of the distal sheath 24 abuts the retainer 27 when the distal sheath is in the closed position fully covering the compartment 23. The proximal edge 29 is spaced apart from the retainer 27 when the compartment 23 is at least partially uncovered, as shown in FIG. 1A.

A marker cage 30 is located circumferentially about the support shaft 21 and is operable for movement between a collapsed condition inside of distal sheath 24 when the distal sheath is in the closed position, and an expanded condition when the distal sheath is in the open position at least partially uncovering the compartment 23. The marker cage 30 is adapted to radially expand along with and inside of the annulus portion 10 of the prosthetic heart valve 1. The marker cage 30 includes a plurality of ribs 33 joined at their proximal ends to a tubular ring 31, and at their distal ends to a tubular ring 32. Rings 31 and 32 extend around the circumference of the support shaft 21. The ring 32 may be fixed relative to the support shaft 21 and the retainer 25, while the ring 31 may be slidable along the support shaft proximally and distally during radial expanding and collapsing of the marker cage 30, thereby permitting the distance between the distal and proximal ends to shorten upon radial expansion of the marker cage, and to lengthen upon radial collapsing of the marker cage. Alternatively, the ring 31 may be fixed relative to the support shaft 21 and the retainer 27, while the ring 32 may be mounted for relative sliding movement along the support shaft.

Figure 2A:
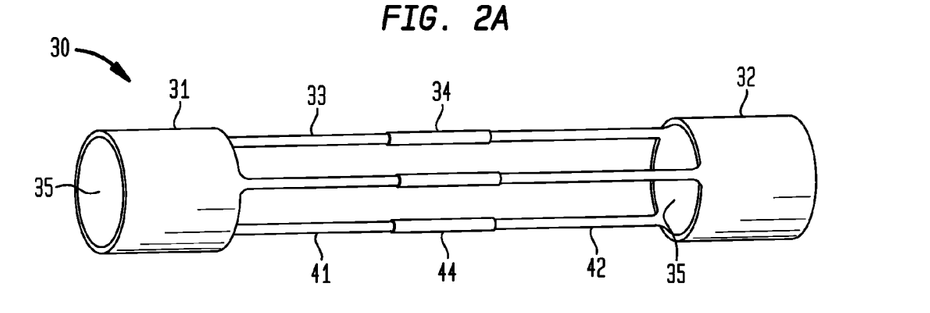
FIG. 2A is a highly schematic perspective view of an expandable cage portion of the delivery device of FIG. 1A, shown in a collapsed condition.

Referring now to FIG. 1B, each rib 33 of the marker cage 30 includes a proximal portion 41 adjacent the ring 31, a distal portion 42 adjacent the ring 32, and a medial portion extending between the proximal and distal portions. A marker 34 may be formed on or around the medial portion 44 of each rib 33, or selected ones of the ribs 33. In the collapsed condition (e.g., as shown in FIG. 2A), each rib 33 extends along the support shaft 21, such that the ribs may be substantially parallel to the support shaft. In the expanded condition, the proximal portion 41 of each rib 33 may project away from the longitudinal axis of the support shaft 21 at an acute angle A, the distal portion 42 of each rib may project away from the longitudinal axis of the support shaft at an acute angle B, and the medial portion 44 may be substantially parallel to the support shaft. The acute angles A and B may be approximately equal, or they may be different from one another, for example, where the proximal portion 41 of each rib has a different length than the distal portion 42 of each rib, or where the marker cage 30 is constructed so that the medial portion 44 is oriented at an angle to the support shaft 21 in the fully expanded condition.

Referring now to FIG. 2A, the marker cage 30 may be formed from a memory material tube, such as a nitinol tube, having an aperture 35 extending therethrough. For example, a single memory material tube may be laser cut to remove material, thereby creating the three ribs 33 extending between the rings 31 and 32. In a particular embodiment, the rings 31 and 32 and the ribs 33 may be formed separately and joined together to create the marker cage 30. The markers 34 may be applied to the respective medial portions 44, for example, by using a press fit of the marker onto the medial portion, electroplating the markers onto the medial portions, using an adhesive therebetween, or using another application mechanism. Each marker 34 may include a material selected from the group consisting of gold, platinum, nitinol, and combinations thereof, or another metallic material, and may be radiopaque, i.e., the markers may have enhanced visibility to a user under fluoroscopy.

Figure 2B:
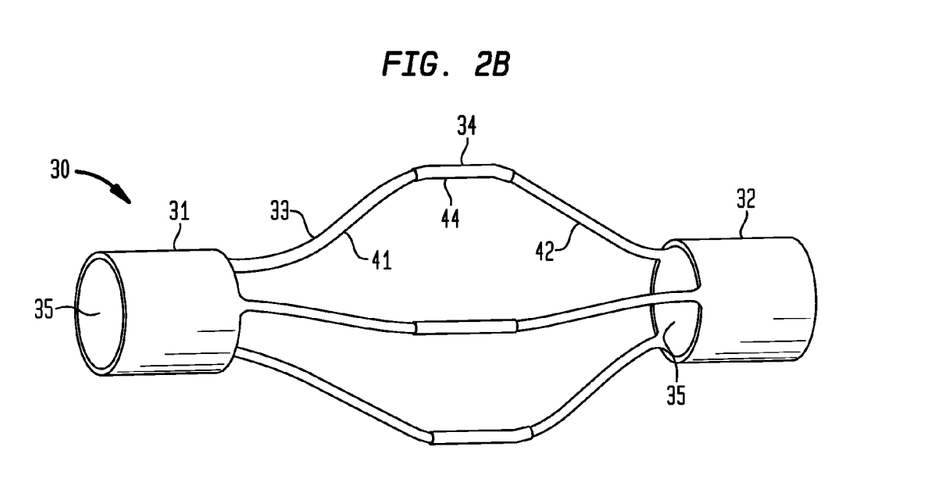
FIG. 2B is a highly schematic perspective view of the expandable cage of FIG. 2A, shown in an expanded condition.

When the distal sheath 24 is in the closed position, the marker cage 30 may be in the collapsed condition shown in FIG. 2A. The marker cage 30 may be biased to take the shape of the expanded condition shown in FIG. 2B, such that as the distal sheath 24 moves from the closed position to the open position, the marker cage changes shape from the collapsed condition to the expanded condition.

Figure 3A:
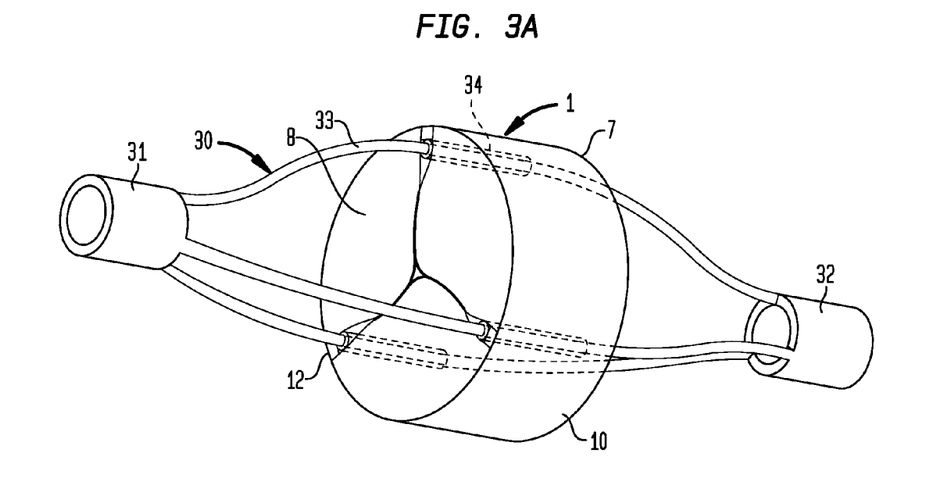
FIG. 3A is an enlarged highly schematic perspective view of the expandable cage of FIG. 2A engaged in the collapsible prosthetic heart valve of FIG. 1C, shown in an expanded condition.
Figure 3B:
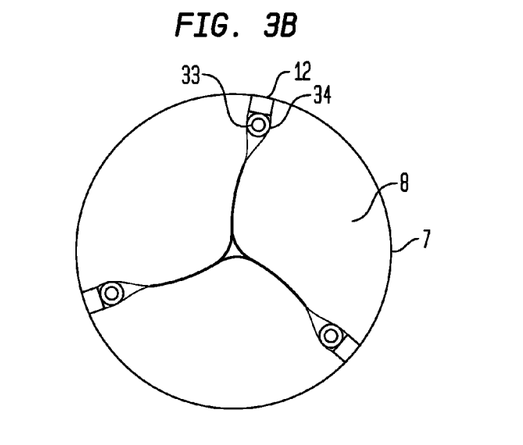
FIG. 3B is an enlarged highly schematic end view of the expandable cage and collapsible prosthetic heart valve of FIG. 3A, with portions removed to illustrate the engagement between the cage and the valve.

Referring now to FIGS. 3A and 3B, the marker cage 30 is shown in the expanded condition engaged in the annulus portion 10 of the collapsible prosthetic heart valve 1. In the expanded condition, three ribs 33 extend through the prosthetic heart valve 1 in respective spaces between adjacent leaflets 8 near the tissue cuff 7. As shown, commissure attachment material 12, such as tissue and suture bulk where cusps of the leaflets come together, may extend between each rib 33 and the tissue cuff 7.

Each rib 33 preferably is located between adjacent leaflets 8 to provide a substantially fixed location of each marker 34 relative to the leaflets during deployment of the prosthetic heart valve 1, so that the axial and rotational location of the prosthetic heart valve relative to a patient's native annulus can be visualized using fluoroscopy. The engagement of each rib 33 between adjacent leaflets 8 at a substantially fixed location adjacent the tissue cuff 7 and/or adjacent the commissure attachment material 12 may minimize the risk of the ribs damaging the leaflets during deployment of the prosthetic heart valve 1 due to incidental contact between the ribs and the leaflets.

The memory bias of the marker cage 30 can be predetermined, such that, when no force is applied to the marker cage to obstruct radial expansion of the marker cage, the marker cage may expand to a generally cylindrical shape having a maximum diameter, with each marker 34 lying in the wall of the cylinder. It is preferable that such maximum diameter be equal to or greater than the fully expanded diameter of the prosthetic heart valve 1 (i.e., the diameter of the valve in a radially unconstrained state). In such event, the memory bias of the marker cage 30 will provide a radially-outward force of the markers 34 against the tissue cuff 7 and/or the commissure attachment material 12 at all times before and during deployment of the valve, thereby helping maintain the substantially fixed location of each marker 34 relative to the leaflets 8. In a particular embodiment, each marker 34 can be oriented substantially parallel to a longitudinal axis of the tissue cuff 7.

To use the delivery device 13 to insert the collapsible prosthetic heart valve 1 into a patient at a desired location, the user can first load the valve into the compartment 23 by sliding the valve over the distal sheath 24 toward the compartment 23, and then sliding the valve over the marker cage 30 so that the ribs 33 thereof engage between the leaflets 8. The aortic end 6 of the valve 1 may then be attached to the retainer 25, and the valve may be crimped to reduce its diameter such that it fits inside of the distal sheath 24, the crimping of the valve also radially compressing the marker cage 30 into the collapsed condition. Examples of suitable retainers and methods of coupling prosthetic valves to such retainers are shown and described in United States Patent Application Publication No. 2012/0078350, the disclosure of which is hereby incorporated by reference herein.

With the distal sheath 24 in the closed position, the user can insert the catheter assembly 16 into a patient, for example, through an incision in the apex of the patient's heart, advancing the catheter assembly until the distal sheath is positioned at the native annulus of the patient. The axial and rotational position of the valve 1 relative to the patient's native annulus can be determined by visualizing the markers 34 using fluoroscopy. If the position of the valve 1 is acceptable to the user, the valve may then be deployed at the desired location by sliding the inner shaft 26 and the distal sheath 24 distally relative to the support shaft 21 and the valve 1 mounted thereabout, so that the valve will begin to become uncovered and to self-expand. During the radial expansion of the valve 1, the marker cage 30 also radially expands, thereby moving from the collapsed condition towards the expanded condition and maintaining the position of the markers 34 between the leaflets 8 and adjacent the tissue cuff 7 and/or the commissure attachment material 12, so that a user can continue to visualize the position of the valve during deployment. As shown in FIG. 1A, the marker cage 30 may be fully radially expanded while the valve 1 is only partially deployed (i.e., the retention members 9 of the valve are still engaged in the retainer 25).

While the valve is partially deployed, fluoroscopy may be used to determine the position of the valve 1 inside the patient by viewing the markers 34. If a user desires to resheathe the valve 1 to reposition the valve before full deployment, the user can slide the inner shaft 26 and the distal sheath 24 proximally relative to the support shaft 21, thereby radially compressing the valve back inside the distal sheath. During resheathing of the valve 1, the marker cage 30 also radially compresses to the collapsed condition while maintaining the position of the markers 34 between the leaflets 8 and adjacent the tissue cuff 7 and/or the commissure attachment material 12. When desired, a user can continue deployment by sliding the inner shaft 26 and the distal sheath 24 distally relative to the support shaft 21 and the valve 1 in the compartment 23 until the valve is released from the delivery device 13.

After the valve 1 has been released from the delivery device 13 and is fully expanded, the ribs 33 of the marker cage 30 preferably remain engaged in the valve between the leaflets 8 and adjacent the tissue cuff 7 and/or the commissure attachment material 12. To radially collapse the marker cage 30 so that the delivery device 13 can be withdrawn from the valve 1, a user may slide the inner shaft 26 and the distal sheath 24 proximally relative to the support shaft 21 and the marker cage 30 attached thereto. The proximal edge 29 of the distal sheath 24 will slide within the aortic portion 11 of the valve 1 until it contacts the proximal portions 42 of the ribs 33, whereupon the distal sheath may apply a radially compressive force to the ribs, thereby moving the ribs away from the valve and toward the support shaft 21 as the marker cage 30 is compressed to the collapsed condition within the distal sheath. Preferably, the compressing of the marker cage 30 may be performed during the portion of the heart beat cycle when blood is flowing through the leaflets 8 of the valve 1 to thereby minimize contact between the ribs 33 and the leaflets.

Figure 4:
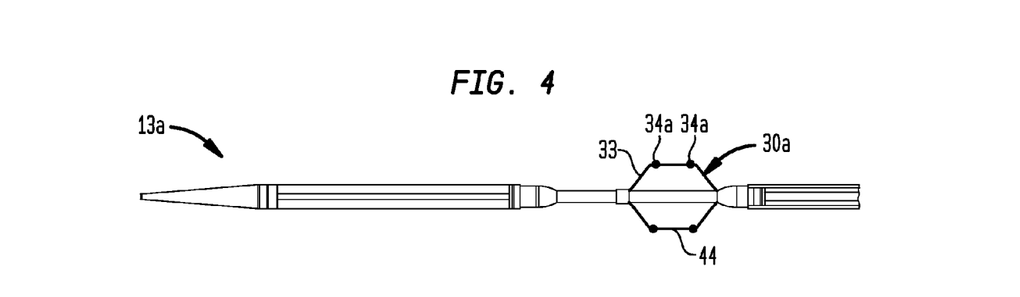
FIG. 4 is a side elevational view of the distal portion of another embodiment of a transapical delivery device for a collapsible prosthetic heart valve according to the present invention.

A transapical delivery device 13a for the collapsible prosthetic heart valve 1 in accordance with another embodiment of the invention is shown in FIG. 4. The delivery device 13a is similar to the delivery device 13 described above, except that each rib 33 of a marker cage 30a includes two markers 34a rather than a single marker. Each rib 33 has a marker 34a located at the distal and proximal ends of its medial portion 44.

Figure 5:
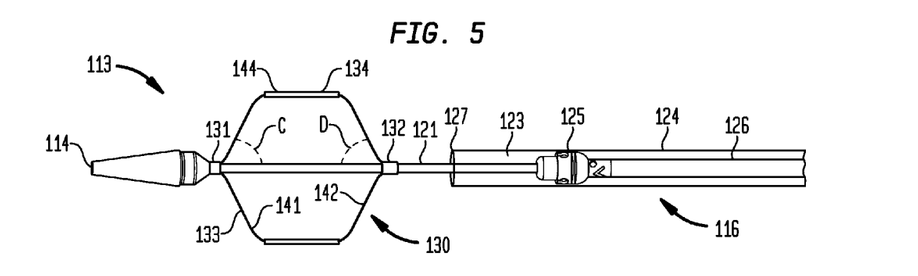
FIG. 5 is a side elevational view of the distal portion of one embodiment of a transfemoral delivery device for a collapsible prosthetic heart valve according to the present invention.

Referring now to FIG. 5, an exemplary transfemoral delivery device 113 for the collapsible prosthetic heart valve 1 (or other types of collapsible stents) extends from an atraumatic tip 114 at the distal end of the device to a proximal end (not shown), and includes a catheter assembly 116 for delivering the heart valve to and deploying the heart valve at a target location. The catheter assembly 116 is adapted to receive the collapsible prosthetic heart valve 1 in an assembled condition in a compartment 123 defined around a support shaft 121. A distal sheath 124 is operable for sliding movement between a closed position covering the prosthetic heart valve 1 and maintaining it in a collapsed condition, and an open position for deployment of the valve.

The support shaft 121 extends between the atraumatic tip 114 and a retainer 125 affixed to the support shaft, which together define the spaced ends of the compartment 123. The retainer 125 is adapted to receive the retention members 9 of the prosthetic heart valve 1 so as to hold the aortic end of the heart valve in assembled relationship with the delivery device 113. The delivery device further includes an inner shaft 126, the distal end of which is connected to the retainer 125, and the proximal end of which can optionally be connected to a hub (not shown) that can be held by a user when sliding the distal sheath 124 relative to the support shaft 121.

The distal sheath 124 surrounds the support shaft 121 when the distal sheath is in the closed position, and is slidable relative to the support shaft such that it can selectively cover or uncover compartment 123. The distal sheath 124 may be connected at its proximal end to a hub (not shown) that can be held by a user. A distal edge 127 of the distal sheath 124 abuts the atraumatic tip 114 when the distal sheath is in the closed position covering the compartment 123. The distal edge 127 is spaced apart from the atraumatic tip 114 when the compartment 123 is at least partially uncovered, as shown in FIG. 5.

The delivery device 113 includes a marker cage 130 that is similar in structure to the marker cage 30 described above. That is, the marker cage 130 includes a plurality of ribs 133 connected at their proximal ends to a ring 132 and at their distal ends to a ring 131. One of the rings 131 and 132 may be fixed relative to the support shaft 121, while the other ring may be slidable relative thereto, thereby facilitating the movement of the marker cage 130 between a collapsed condition covered by the distal sheath 124, and the fully expanded condition shown in FIG. 5. In the expanded condition, a distal portion 141 of each rib 133 may project away from the longitudinal axis of the support shaft 121 at an acute angle C, a proximal portion 142 of each rib may project away from the longitudinal axis of the support shaft at an acute angle D, and a medial portion 144 of each rib may be substantially parallel to the support shaft. The acute angles C and D may be approximately equal, or they may be different from one another as described above.

To use the delivery device 113 to insert the collapsible prosthetic heart valve 1 into a patient at a desired location, the user can first load the valve into the compartment 123 so that the ribs 133 of the marker cage 130 engage between the leaflets 8, in a manner similar to that described above with reference to FIG. 1A. With the distal sheath 124 in the closed position, the user can insert the catheter assembly 116 into a patient, for example, through an incision in the patient's femoral artery, advancing the catheter assembly until the distal sheath 124 is positioned at the native annulus of the patient.

Similar to the device 13 shown in FIG. 1A, the axial and rotational position of the valve 1 relative to the patient's native annulus can be determined by visualizing the markers 134 using fluoroscopy. If the position of the valve 1 is acceptable to the user, the valve may then be deployed at the desired location by sliding the distal sheath 124 proximally relative to the support shaft 121 and the valve mounted thereabout, so that the valve will begin to become uncovered and to self-expand. During the radial expansion of the valve 1, the marker cage 130 also radially expands, thereby moving from the collapsed condition towards the expanded condition and maintaining the position of the markers 134 between the leaflets 8 of the valve.

While the valve is partially deployed, fluoroscopy may be used to determine the position of the valve inside the patient by viewing the markers 134. If a user desires to resheathe the valve 1, the user can slide the distal sheath 124 distally relative to the support shaft 121, thereby radially compressing the valve back inside the distal sheath. During resheathing of the valve 1, the marker cage 130 also radially compresses to the collapsed condition while maintaining the position of the markers 134 between the leaflets 8 of the valve. When desired, a user can continue deployment by sliding the distal sheath 124 proximally relative to the support shaft 121 and the valve 1 mounted in the compartment 123 until the valve is released from the delivery device 113.

To radially collapse the marker cage 130 so that the delivery device 113 can be withdrawn from the valve 1, a user may slide the distal sheath 124 distally relative to the support shaft 121 and the marker cage 130 attached thereto. The distal edge 127 of the distal sheath 124 will slide within the aortic portion 11 of the valve 1 until it contacts the proximal portions 142 of the ribs 133, whereupon the distal sheath may apply a radially compressive force to the ribs, thereby moving the ribs away from the valve and toward the support shaft 121 as the marker cage 130 is compressed to the collapsed condition within the distal sheath.

Figure 6:
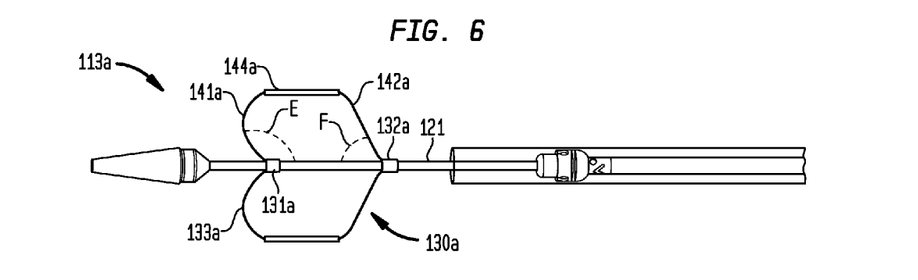
FIG. 6 is a side elevational view of the distal portion of another embodiment of a transfemoral delivery device for a collapsible prosthetic heart valve according to the present invention.

Referring now to FIG. 6, an exemplary transfemoral delivery device 113a for the collapsible prosthetic heart valve 1 is shown with an alternate rib arrangement. The delivery device 113a has a marker cage 130a including ribs 133a, each rib 133a having a curved distal portion 141a. At least one of the distal ring 131a and the proximal ring 132a of the marker cage 130a is fixedly connected to the support shaft 121. When only one of the distal and proximal rings is fixedly connected to the support shaft 121, the other ring may be mounted for relative sliding movement along the support shaft, in a similar manner as discussed above with reference to FIG. 1A. In the collapsed condition of the marker cage 130a, the distal portion 141a of each rib 133a may be folded at an inflection point along the distal portion. In the expanded condition, the distal portion 141a of each rib 133a may project away from the support shaft 121 at an obtuse angle E, the proximal portion 142a of each rib may project away from the support shaft at an acute angle F, and the medial portion 144a may be substantially parallel to the support shaft.

Figure 7:
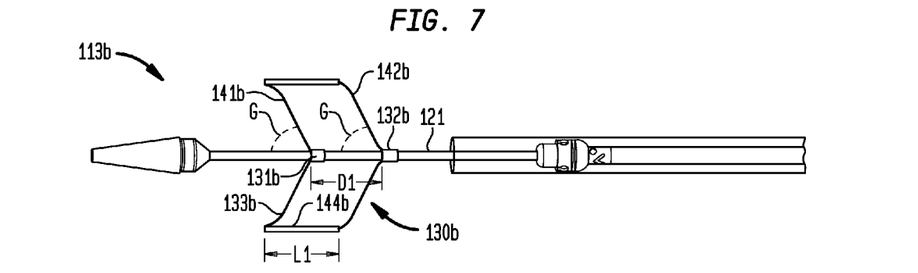
FIG. 7 is a side elevational view of the distal portion of yet another embodiment of a transfemoral delivery device for a collapsible prosthetic heart valve according to the present invention.

Referring now to FIG. 7, an exemplary transfemoral delivery device 113b for the collapsible prosthetic heart valve 1 is shown with another rib arrangement. At least one of the distal ring 131b and the proximal ring 132b of the marker cage 130b is fixedly connected to the support shaft 121. When only one of the distal and proximal rings is fixedly connected to the support shaft 121, the other ring may be mounted for relative sliding movement along the support shaft, similar to the embodiment of FIG. 1A. In embodiments in which both the distal and proximal rings are fixedly connected to the support shaft 121 and the distal portions 141b and the proximal portions 142b of the ribs are about equal in length, it is preferable that the distance D1 between the points of attachment of the ribs 133b to the rings 131b and 132b is approximately equal to the length L1 of the medial portions 144b of the ribs, such that the medial portions may remain approximately parallel to the support shaft 121 as the marker cage 130b moves between the collapsed and expanded conditions. In the expanded condition, the distal portion 141b and the proximal portion 142b of each rib 133b may be substantially parallel to one another, with both portions oriented in the distal direction so as to define an acute angle G between these portions and the support shaft 121.

Figure 8:
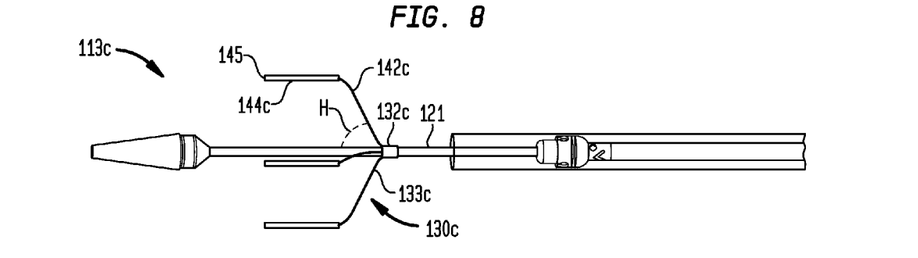
FIG. 8 is a side elevational view of the distal portion of still another embodiment of a transfemoral delivery device for a collapsible prosthetic heart valve according to the present invention.

Referring now to FIG. 8, an exemplary transfemoral delivery device 113c for the collapsible prosthetic heart valve 1 is shown with yet another rib arrangement. The delivery device 113c has a marker cage 130c including ribs 133c, each rib 133c having a proximal portion 142c connected at one end to a proximal ring 132c that is fixedly connected to the support shaft 121. The other end of the proximal portion 142c is connected to a medial portion 144c that terminates in a free end 145. That is, each medial portion 144c is attached in a cantilevered fashion to a single ring 132c. In the expanded condition, the proximal portion 142c of each rib may project away from the support shaft 121 at an acute angle E1, and the medial portion 144c may be substantially parallel to the support shaft.

In the delivery devices shown in FIGS. 1A and 4-8, particular structures are shown that include markers that are adapted to be engaged in a collapsible prosthetic heart valve and to be visible to a user or imaging system during fluoroscopy. The invention also contemplates the use of any alternative markers and marker cage structures that provide such engagement in a collapsible prosthetic heart valve and visibility during fluoroscopy. For example, any number of ribs may be provided in the marker cage to allow engagement of markers with a collapsible prosthetic heart valve, and such ribs may have any shape and may project at any angle relative to the longitudinal axis of the inner shaft. It is preferable that the number of ribs be equal to the number of leaflets of the collapsible prosthetic heart valve to be deployed, so that each rib may be engaged between adjacent valve leaflets. It is also preferable that the marker cage include at least two radiopaque markers, although it is not necessary that a marker be included on or within each rib.

The invention also contemplates the use of alternative marker structures that have any length, shape, and configuration. For example, any number of markers may be provided on a single marker cage rib, including two (e.g., the markers 34a shown in FIG. 4), three, four, five, or more. Each marker and each rib medial portion may be straight (as shown in the figures) or curved, may have a zig-zag shape, or may have a combination of shapes. Each marker and each rib medial portion may project at any fixed or variable angle relative to the longitudinal axis of the inner shaft. It is preferable that the angle of the medial portion of each rib be approximately parallel to the angle of the tissue cuff of the collapsible prosthetic heart valve to be deployed, such that each rib may be better engaged within the valve. In one embodiment, one or more partial or entire ribs may be radiopaque or partially or fully surrounded by a radiopaque marker material, such that one or more such ribs may serve as markers. In another embodiment, the entire marker cage or a portion thereof may be radiopaque or partially or fully surrounded by a radiopaque marker material, such that at least a portion of the marker cage may serve as a marker.

Although the various delivery devices have been described herein in connection with the use of a self-expanding marker cage in the deployment of a prosthetic valve having a self-expanding stent structure, all of the delivery devices may include a marker cage that is expandable and/or collapsible by another mechanism, such as a balloon-expansion mechanism, for use in deploying a prosthetic valve that does not have a self-expanding stent structure. Furthermore, rather than being used in the deployment of prosthetic valves having a collapsible stent structure, all of the delivery devices may be used for other purposes. In particular, the various delivery devices may be used to retain and deliver conventional collapsible stents that do not contain a valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, while the marker cages herein have been described as having a plurality of ribs, it is contemplated that each of the marker cages may be formed with a single rib or any number of ribs greater than one. Furthermore, although the invention herein has been described with reference to particular embodiments in which the annulus end of a prosthetic valve is deployed first, it is to be understood that the invention contemplates embodiments in which the aortic end of a valve is deployed first. In such embodiments, the annulus end of the stent portion of the valve may be engaged with a retainer, while the aortic end of the stent may be remote from the retainer and may be unsheathed first.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A medical combination, comprising:
a delivery device, the delivery device comprising:
  a support shaft around which a compartment is defined;
  a distal sheath adapted to selectively cover and uncover the compartment;
  a marker cage having a collapsed condition when the distal sheath covers the compartment and an expanded condition when the compartment is uncovered, the marker cage having a first end fixedly connected to the support shaft and a second end opposite from the first end, and a plurality of ribs each having a fixed end connected to the first end, the plurality of ribs being disposed around a longitudinal axis of the support shaft; and
at least one radiopaque marker on the marker cage, each rib having at least one of the radiopaque markers, each radiopaque marker disposed on the corresponding rib and spaced apart from each of the first and second ends of the marker cage; and
a collapsible prosthetic heart valve mounted in the compartment of the delivery device, the prosthetic heart valve including:
  a stent portion comprising stent members having a plurality of spaces therebetween;
  a tissue cuff extending about an inner circumference of the stent portion; and
  a plurality leaflets extending inwardly from the tissue cuff, with their free edges in a coapting relationship,
wherein each radiopaque marker is engaged between adjacent leaflets of the valve, and the number of ribs of the marker cage is equal to the number of leaflets of the valve, and
wherein the prosthetic heart valve is self-expanding and the marker cage is self-expanding, such that both the prosthetic heart valve and the marker cage in the collapsed condition are adapted to self-expand together when no force is applied to obstruct radial expansion of the prosthetic heart valve.

2. The medical combination of claim 1, wherein each radiopaque marker includes a material selected from the group consisting of gold, platinum, nitinol, and combinations thereof.

3. The medical combination of claim 1, wherein the marker cage is formed from a memory material tube having an aperture extending therethrough.

4. The medical combination of claim 1, wherein the marker cage has a second end slidably connected to the support shaft, and the at least one rib has another end connected to the second end.

5. The medical combination of claim 1, wherein the second end of the marker cage is fixedly connected to the support shaft, and each of the plurality of ribs has another end connected to the second end.

6. The medical combination of claim 1, wherein each of the plurality of ribs has a free end opposite the fixed end.

7. The medical combination of claim 1, wherein the prosthetic heart valve includes a tissue cuff having a longitudinal axis, and the at least one marker is adapted to be oriented substantially parallel to the longitudinal axis in the assembled condition.

8. The medical combination of claim 1, wherein the marker cage has an expanded diameter that is greater than an expanded diameter of the prosthetic heart valve.

9. The medical combination of claim 1, wherein the at least one rib has first and second legs, the first leg having one end connected to the first end of the marker cage and another end, the second leg having a first end connected to the another end of the first leg and a second end, wherein the second leg extends substantially parallel to the support shaft when the marker cage is in the expanded condition.

10. The medical combination of claim 9, wherein the marker cage has a second end slidably connected to the support shaft, and the at least one rib further includes a third leg having one end connected to the second end of the second leg and another end connected to the second end of the marker cage, wherein the first and third legs of the at least one rib extend in substantially opposite transverse directions to the support shaft when the marker cage is in the expanded condition.

11. A medical combination, comprising:
a marker cage for use in deployment of a collapsible prosthetic heart valve, the marker cage comprising:
a first end and a second end opposite from the first end;
a plurality of ribs each having one end connected to the first end, the plurality of ribs being disposed around a longitudinal axis of the marker cage; and
at least one radiopaque marker, each rib having at least one of the radiopaque markers, each radiopaque marker disposed on the corresponding rib and spaced apart from each of the first and second ends of the marker cage,
the marker cage having a collapsed condition and an expanded condition; and
a collapsible prosthetic heart valve mounted on the marker cage, the prosthetic heart valve including:
a stent portion comprising stent members having a plurality of spaces therebetween;
a tissue cuff extending about an inner circumference of the stent portion; and
a plurality of leaflets extending inwardly from the tissue cuff, with their free edges in a coapting relationship,
wherein each radiopaque marker is engaged between adjacent leaflets of the valve, and the number of ribs of the marker cage is equal to the number of leaflets of the valve, and
wherein the prosthetic heart valve is self-expanding and the marker cage is self-expanding, such that both the prosthetic heart valve and the marker cage in the collapsed condition are adapted to self-expand together when no force is applied to obstruct radial expansion of the prosthetic heart valve.

12. The medical combination of claim 11, wherein each radiopaque marker includes a material selected from the group consisting of gold, platinum, nitinol, and combinations thereof.

13. The medical combination of claim 11, wherein the marker cage is formed from a memory material tube having an aperture extending therethrough.

14. The medical combination of claim 11, further comprising a second end, the at least one rib having another end connected to the second end.

15. The medical combination of claim 11, wherein each of the plurality of ribs has a free end opposite the one end.

16. The medical combination of claim 11, wherein the marker cage has an expanded diameter that is greater than an expanded diameter of the prosthetic heart valve.

17. The medical combination of claim 11, wherein the radiopaque markers are positioned equidistantly from the longitudinal axis in the expanded condition of the marker cage.

18. The medical combination of claim 11, wherein the at least one rib has first and second legs, the first leg having one end connected to the first end of the marker cage and another end, the second leg having a first end connected to the another end of the first leg and a second end, wherein the second leg extends substantially parallel to a longitudinal axis of the marker cage when the marker cage is in the expanded condition.

19. The medical combination of claim 18, wherein the marker cage has a second end, and the at least one rib further includes a third leg having one end connected to the second end of the second leg and another end connected to the second end of the marker cage, wherein the first and third legs of the at least one rib extend in substantially opposite transverse directions to the longitudinal axis when the marker cage is in the expanded condition.

\* \* \* \* \*